(12) United States Patent
Kasprzak et al.

(10) Patent No.: US 8,753,268 B2
(45) Date of Patent: Jun. 17, 2014

(54) ACCESS PORT (71) Applicant: Cook Medical Technologies LLC, Bloomington, IN (US)

(72) Inventors: Piotr Miroslaw Kasprzak, Regensburg (DE); Werner Dieter Ducke, Eight Mile Plains (AU); Blayne A. Roeder, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/798,522

(22) Filed: Mar. 13, 2013

(65) Prior Publication Data
US 2013/0331655 A1 Dec. 12, 2013

(30) Foreign Application Priority Data
May 8, 2012 (AU) ................................ 2012202669

(51) Int. Cl.
*A61B 1/32* (2006.01)
(52) U.S. Cl.
USPC .......................................... 600/208; 600/205
(58) Field of Classification Search
USPC ................................................. 600/205–208
See application file for complete search history.

(56) References Cited

U.S. PATENT DOCUMENTS

| | | | |
|---|---|---|---|
| 4,929,235 A | 5/1990 | Merry et al. | |
| 7,172,580 B2 | 2/2007 | Hruska et al. | |
| 7,637,863 B2 | 12/2009 | Deal et al. | |
| 2003/0050604 A1 | 3/2003 | Lui et al. | |
| 2005/0020981 A1 | 1/2005 | Kurth | |
| 2009/0012476 A1 | 1/2009 | Catlin | |
| 2009/0287164 A1* | 11/2009 | Goode et al. | 604/256 |

FOREIGN PATENT DOCUMENTS

WO 2011116308 A1 9/2011

* cited by examiner

*Primary Examiner* — Sameh Boles
(74) *Attorney, Agent, or Firm* — Richard J. Godlewski (57) ABSTRACT

An endoscopic access port and sheath assembly or laparoscopic port (10) comprises a sheath (12) and a haemostatic valve. The sheath has an elongate tubular body and a sheath lumen through it. The haemostatic valve comprising a housing (14), the housing comprises a tubular body with an internal lumen (18) and a first end and a second end. The first end is connected to the sheath and the sheath lumen and the internal lumen are in fluid communication. The second end of the housing has an access port. There is a substantially cylindrical valve assembly (27) within the housing at the second end of the housing. The substantially cylindrical valve assembly is formed from a plurality of valve segments (28). Each valve segment has an elongate body being in cross section a sector of a circle. Each valve segment is formed from a resilient material. The plurality of valve segments when assembled form the substantially cylindrical valve assembly and define between each other a plurality resilient interface regions (29) to receive and grip a medical device between them in use.

15 Claims, 5 Drawing Sheets

ACCESS PORT

TECHNICAL FIELD

This invention relates to a medical device and more particularly to a device for the facilitation of transcutaneous or endovascular delivery of medical devices.

BACKGROUND OF THE INVENTION

This invention will be discussed in particular in relation to the delivery and cannulation of thoracoabdominal stent grafts but the invention is not so limited. It may also, for instance, be used in relation to a laparoscopic port or access sheath.

Thoracoabdominal aneurysms are particularly difficult to treat due to the inclusion of four branch vessels (celiac artery, superior mesenteric artery, and two renal arteries). Endovascular devices are available which include four branches, but cannulation of each branch independently can be difficult and time consuming, exposing the patient to large amount of contrast and x-rays. Preloaded wires associated with a fenestrated stent graft and a delivery device have been demonstrated to greatly ease the process of cannulating the branches of the device. In the case of thoracoabdominal aneurysm, a fenestrated or side arm stent graft with four preloaded wires with catheters or sheaths are required for the four side branches or fenestrations. Since a preloaded delivery system including four lumens for four catheters or preloaded sheaths in the delivery device would be unacceptably large (28 Fr), an alternative option is to individually cannulate the branches using preloaded guide wires from a brachial access site. To accomplish this, the preloaded wires must be inserted from the femoral access with the main delivery and tracked through the abdominal and thoracic aorta, and out through the brachial artery.

PCT Patent Application Number PCT/US2011/029037 (published as WO 2011/116308) entitled "INTRODUCER WITH EXTENSION" lodged on 18 Mar. 2011 discloses arrangements for delivery of fenestrated or branched stent grafts using delivery devices incorporating preloaded guide wires and the teaching therein is incorporated herein in its entirety.

In one stage in the delivery process using such a device, a number, such as four, guide wires are delivered through the vasculature of a patient to exit at or near a shoulder from an access port to a brachial artery.

Once the preloaded wires are exposed from the sheath in the brachial arteries they are difficult to manage while achieving haemostasis. Two particular challenges arise: the wires can easily become entangled through tracking, and identification of each wire is difficult.

It is to overcome some of these problems that the present invention is directed or to at least provide the practitioner with a useful alternative.

BRIEF DESCRIPTION OF THE INVENTION

The invention disclosed is a valve arrangement for a brachial access port and sheath of the delivery system which separates each of the wires and prevents them from becoming entangled. The valve is generally composed of a number of independent silicone-like leaflets. After exiting the brachial access site, the preloaded wires are each pulled into their own slot or region between the leaflets of the valve. This configuration also allows for the wires to be marked so that the physician does not have to pull on each of them for identification.

In one form the invention comprises an access port and sheath assembly comprising a sheath and a hemostatic valve, the hemostatic valve comprising a housing and a substantially cylindrical valve assembly in the housing, the substantially cylindrical valve assembly comprising a plurality of valve segments, each valve segment comprising an elongate body being in cross section a sector of a circle, whereby the plurality of valve segments when assembled form the substantially cylindrical valve assembly, each valve segment being formed from a resilient material.

Preferably there are four valve segments, each valve segment comprising a substantially quarter of a circle in cross section. Each valve segment can be formed from a silicone rubber.

Each valve segment can comprise an inner part cylindrical portion and an outer annular portion, the inner portion and the outer portion being joined together, the inner portion being formed from a material which is harder or more dense than the material of the outer portion. The inner and outer portion can be co-moulded or one of the portions can be moulded over or within the other portion.

Preferably the substantially cylindrical valve assembly formed from the plurality of valve segments has a length and a diameter and the length is at least the same as the diameter. More preferably the length of the substantially cylindrical valve assembly is from one to two times the diameter of the substantially cylindrical valve assembly. The substantially cylindrical valve assembly can for instance have a length of from 15 to 30 mm and a diameter of from 10 to 15 mm.

There can be further included a flushing port in the housing.

Preferably the sheath is a flexible sheath.

In a preferred embodiment each of the plurality of valve segments comprises an elongate body being in cross section a sector of a circle with a sector of a circle flange extending out radially from one end thereof.

Alternatively the cylindrical valve assembly comprises the plurality of valve segments and a circular flange extending out radially from one end thereof and joining the valve segments.

In an alternative form the invention comprises an endovascular access port and sheath assembly comprising a sheath and a hemostatic valve;

the sheath comprising an elongate tubular body and a sheath lumen therethrough;

the hemostatic valve comprising a housing, the housing comprising a tubular body with an internal lumen and a first end and a second end, the first end being connected to the sheath and the sheath lumen and the internal lumen being in fluid communication, the second end of the housing comprising an access port;

a substantially cylindrical valve assembly within the housing at the second end of the housing and closing the access port, the substantially cylindrical valve assembly comprising a plurality of valve segments, each valve segment comprising an elongate body being in cross section a sector of a circle, each valve segment being formed from a resilient material, whereby the plurality of valve segments when assembled form the substantially cylindrical valve assembly and defining between adjacent valve segments a plurality resilient interface regions to receive and grip a medical device therebetween in use.

Preferably there are four valve segments, each valve segment comprising a substantially quarter of a circle in cross section and thereby defining four of the resilient interface regions, each resilient interface region arranged to grip the medical device in use.

Preferably each valve segment is formed from a silicone rubber.

Preferably the housing comprises a shoulder intermediate the first end and the second end of the housing and the substantially cylindrical valve assembly comprises a first valve end and a second valve end and the first valve end is engaged against the shoulder and the second valve end is engaged against the access port and is accessible therethrough.

There can be further included a flushing port in the housing, the flushing port being in fluid communication with the internal lumen between the shoulder and the first end of the housing.

In an alternative form the invention comprises a laparoscopic port, the laparoscopic port comprising a hemostatic valve;

the hemostatic valve comprising a housing, the housing comprising a tubular body with an internal lumen and a first end and a second end, the first end of the housing comprising an access port;

a substantially cylindrical valve assembly within the housing at the first end of the housing, the substantially cylindrical valve assembly comprising a plurality of valve segments, each valve segment comprising an elongate body being in cross section a sector of a circle, each valve segment being formed from a resilient material, whereby the plurality of valve segments when assembled form the substantially cylindrical valve assembly and defining between adjacent valve segments a plurality resilient interface regions to receive and grip a medical device therebetween in use.

BRIEF DESCRIPTION OF THE DRAWING

This then generally describes the invention but to assist with understanding reference will now be made to the accompanying drawings which show a preferred embodiment of the invention.

In the drawings.

DESCRIPTION OF PREFERRED EMBODIMENTS

Figure 1:
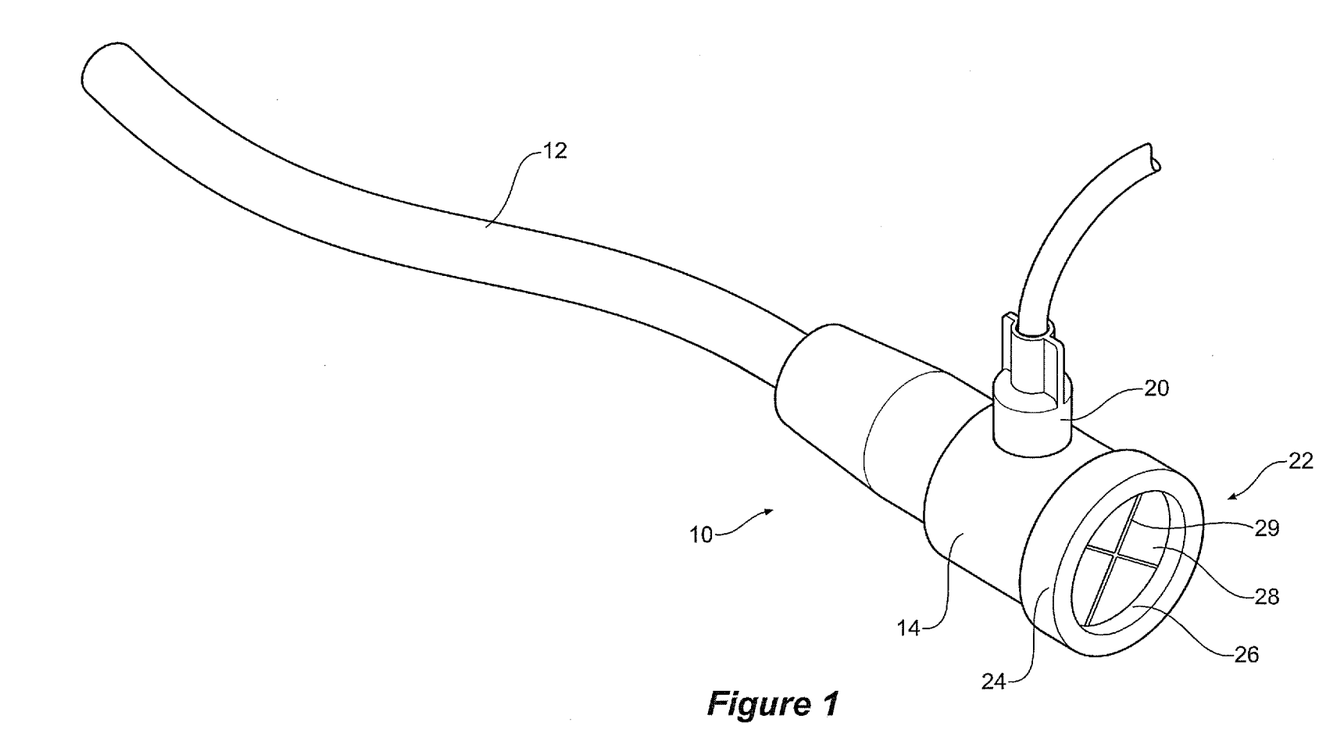
FIG. 1 shows an endovascular access sheath according to one embodiment the present invention.
Figures 2, 3A:
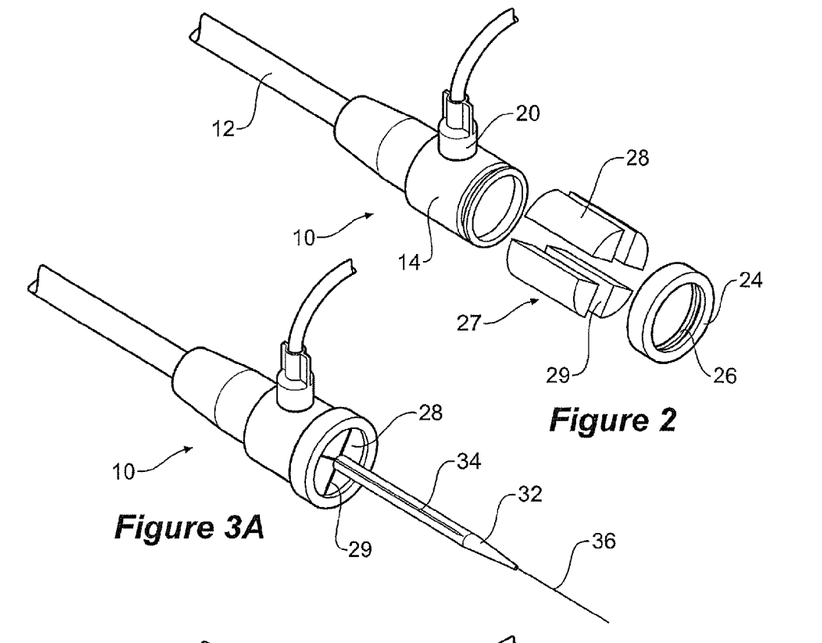
FIG. 2 shows the endovascular access sheath of FIG. 1 dismantled to show the parts.
FIGS. 3A to 3C show the use of the endovascular access sheath of FIG. 1.

FIGS. 1 and 2 show an endovascular access sheath according to one embodiment the present invention.

Figure 4:
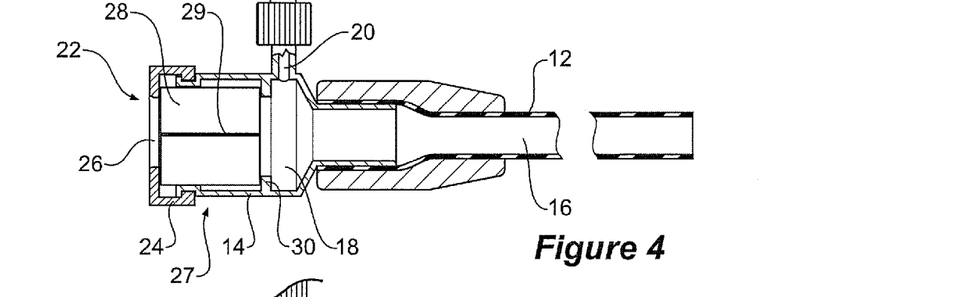
FIG. 4 shows a longitudinal cross sectional view of the endovascular access sheath of FIG. 1.

The access sheath 10 comprises a sheath 12 which is mounted into a housing 14 such that a lumen 16 in the sheath 12 (see FIG. 4) is in fluid communication with a housing lumen 18 in the housing 14. The sheath is formed from a flexible lubricious material such as a polyurethane and may be coated with PTFE. The sheath may be of any desired diameter depending upon its intended application and may be, for instance, 12 French.

The housing 14 has a flushing port 20 which provides fluid access to the housing lumen and sheath lumen to allow fluid flushing in use. The housing 14 has an open end 22 and a retaining cap 24 fits over the open end 22. The cap 24 has an access port or aperture 26. The cap is a snap fit onto the housing but may alternatively be a screw or push fit.

Within the housing at the end 22 is a substantially cylindrical valve assembly 27 which is formed from a plurality of valve pieces 28, in this case four valve pieces 28 (see FIG. 2). Each valve piece or valve segment 28 comprises an elongate body being in cross section a sector of a circle such the plurality of valve segments when assembled form the substantially cylindrical valve assembly 27. Each valve segment is formed from a resilient material such as a soft silicone rubber. The valve segments define between each other a series of resilient interfacial regions 29. By this is meant that the interfacial regions are tight together and provide a seal against blood loss through the hemostatic valve but the valve segments can be separated by something placed between them and then grip that thing and the valve segments as far as possible will seal around the thing placed between them. The thing may be for instance a guide wire for an endovascular procedure, a handle for a laparoscopic tool, a lead for a medical device to be used in a laparoscopic procedure or the like.

It will be noted the substantially cylindrical valve assembly formed from the plurality of valve segments as illustrated has a length and a diameter and that the length is at least the same as the diameter. In a preferred embodiment the length of the substantially cylindrical valve assembly is from one to two times the diameter of the substantially cylindrical valve assembly. For instance the substantially cylindrical valve assembly can for instance have a length of from 15 to 30 mm and a diameter of from 10 to 15 mm.

Within the housing 14 is an annular shoulder 30 (see FIG. 4) against which the cylindrical valve assembly engages to ensure that the valve pieces are held against the cap 24 and against each other. The flushing port 20 opens into the housing lumen between the annular shoulder 30 and the connection with the sheath 12.

Figures 3B, 3C:
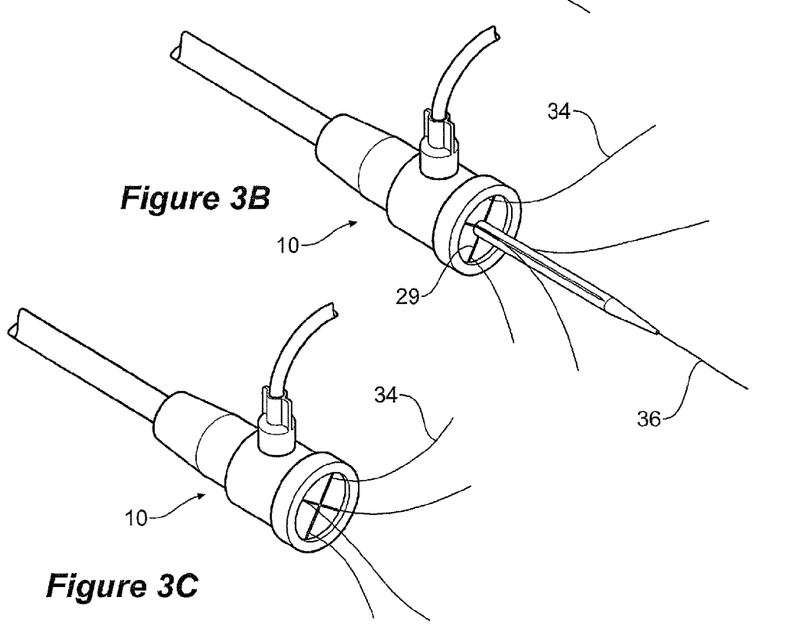
Figure 5A:
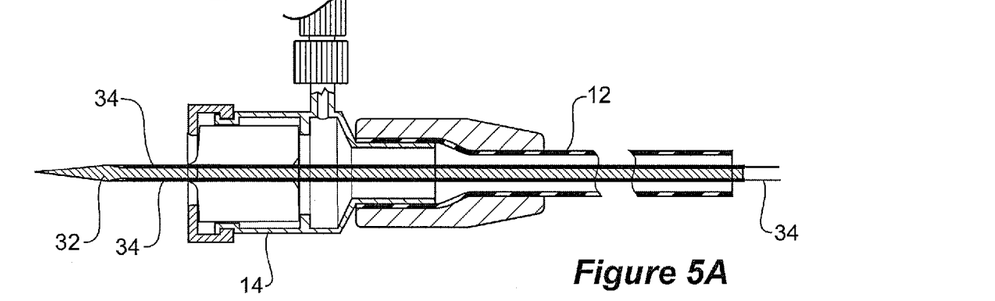
FIGS. 5A to 5C show the use of the endovascular access sheath of FIG. 1 in longitudinal cross sectional view.
Figure 5B:
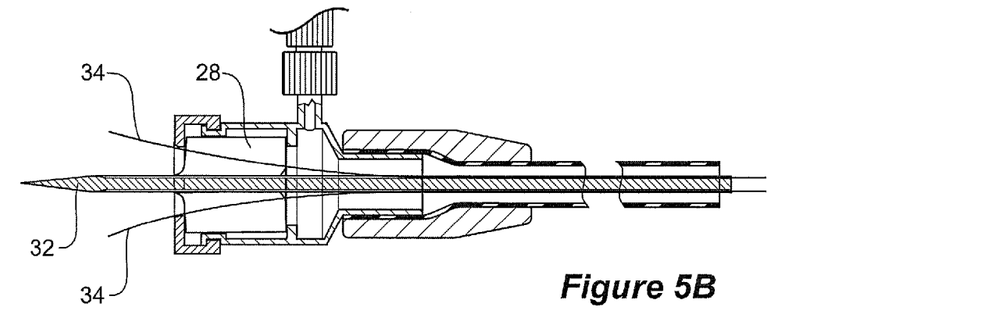
Figure 5C:
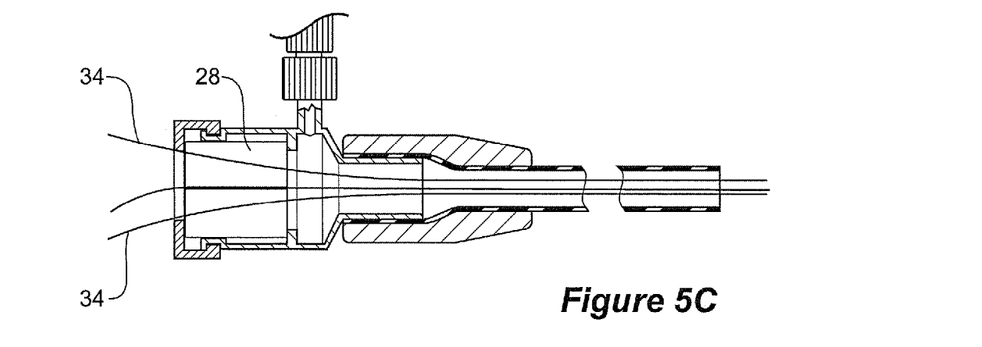

The use of the endovascular sheath of the present invention is shown in FIGS. 3A to 3C and in cross section in FIGS. 5A to 5C.

At the stage of an endovascular procedure shown the endovascular access sheath 10 has been deployed into the left subclavian artery of a patient (not shown) and a length extending module 32 carrying preloaded guide wires 34 has been deployed through the vasculature of a patient over a guide wire 36 and into the sheath 12 to exit out of the cylindrical valve assembly. This stage is shown in FIGS. 3A and 5A. The silicone rubber of the valve pieces 28 are soft enough to be deflected by the nose cone of the length extending module 32 so that the length extending module can pass through it while still providing a hemostatic seal around it.

The length extending module has four grooves along its outside surface and the preloaded guide wires 34 are carried in the grooves. The individual preloaded guide wires are then withdrawn from the respective grooves and pulled into the interfacial regions 29 between respective adjacent valve segments and be retained there. This stage is shown in FIGS. 3B and 5B.

The length extending module can then be withdrawn completely leaving the respective guide wires 34 retained in the respective interfacial regions 29. This stage is shown in FIGS. 3C and 5C. Each preloaded guide wire can then be used separately without the potential problem with tangling with other of the guide wires as they are held apart from each other by the resilient gripping in the respective interfacial regions.

Figure 6:
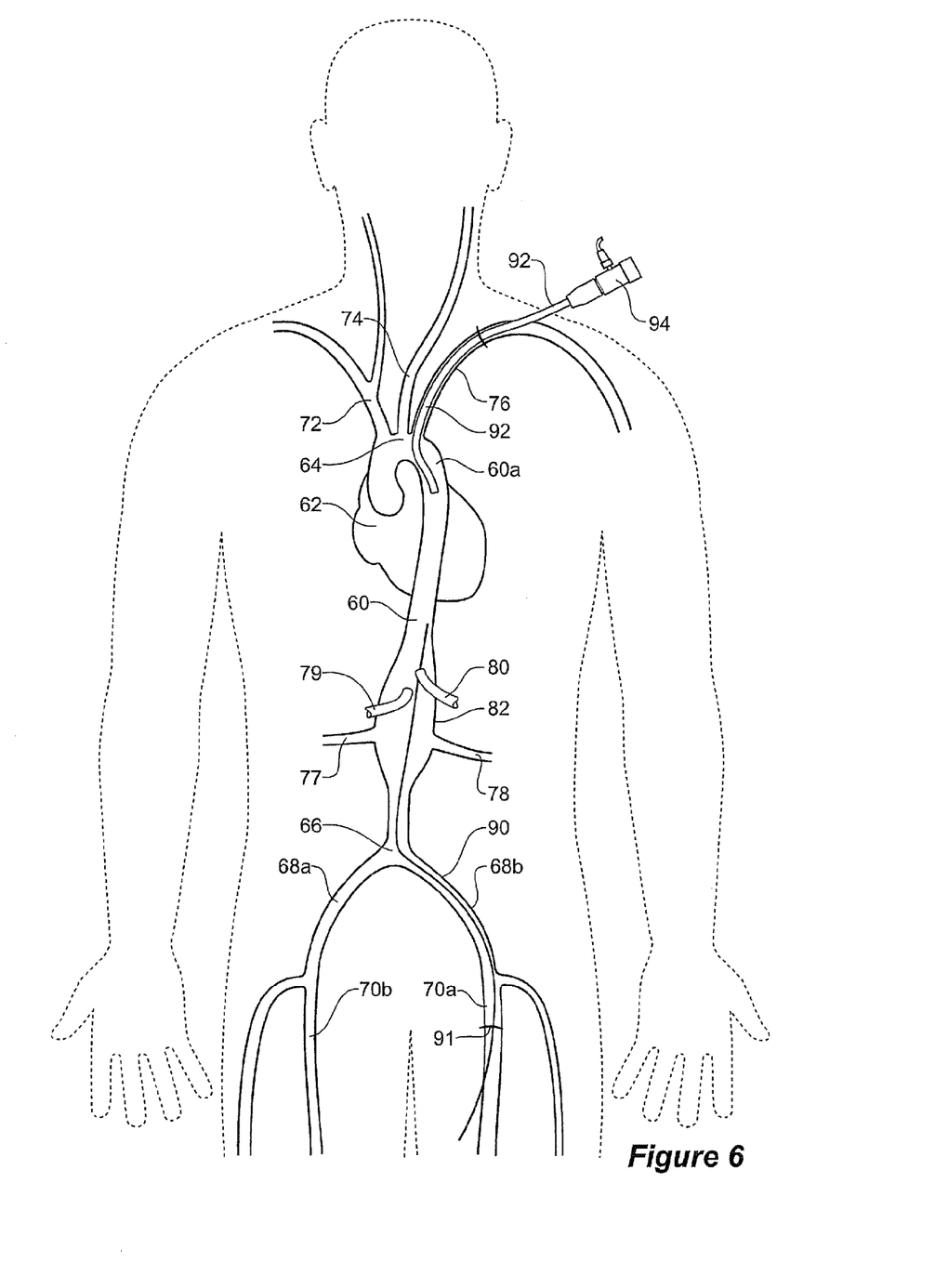
FIG. 6 shows a schematic view of the human body showing one application for the endovascular access sheath or laparoscopic port of the present invention.

FIG. 6 show a schematic view of the vasculature of a human body and one of the uses of the endovascular access sheath of the present invention.

The vasculature shown comprises an aorta 60 extending from a heart 62 over a thoracic arch 64 to an aortic bifurcation 66. At the aortic bifurcation, iliac arteries 68a and 68b extend down to respective femoral arteries 70a and 70b. From the thoracic arch the brachiocephalic artery 72, the left carotid artery 74 and the left subclavian artery 76 extend. In the aorta, there are renal arteries 77 and 78 extending from the aorta and a short distance proximal of them are the superior mesenteric artery 79 and celiac artery 80. These four arteries can generally be referred to as the pararenal or thoracoabdominal arteries. The aorta 60 is depicted with an aneurism 82 which has occurred in the region of the pararenal arteries and it is desired to deploy a stent graft into the aorta to span the aneurism while at the same time allowing catheterisation and side arm deployment into the renal arteries, the superior mesenteric artery and the celiac artery.

In the first stage of the process as is shown in FIG. 6, a guide wire 90 is introduced using the Seldinger technique through a femoral puncture 91 into the femoral artery 70a and extended up through the femoral artery 70a, the iliac artery 68b and into the aorta 60 until it is just proximal of the pararenal arteries. An endovascular access sheath according to the present invention comprising a 12 French catheter or sheath 92 with haemostatic valve assembly or sheath hub 94 is introduced via a brachial puncture using the Seldinger technique into the left subclavian artery 76 and the sheath 92 extended down through the left subclavian artery into the descending aorta 60a. This placement of the access port and sheath assembly according to the present invention enables good management of the preloaded guide wires for the catheterisation and stent grafting of the renal and pararenal arteries.

The full process of stent graft placement in the pararenal region and the catheterisation and stent grafting of the renal and pararenal arteries is disclosed in PCT Patent Application Number PCT/US2011/029037 (published as WO 2011/116308) entitled "INTRODUCER WITH EXTENSION" lodged on 18 Mar. 2011 and the teaching therein is incorporated herein in its entirety.

Figure 7:
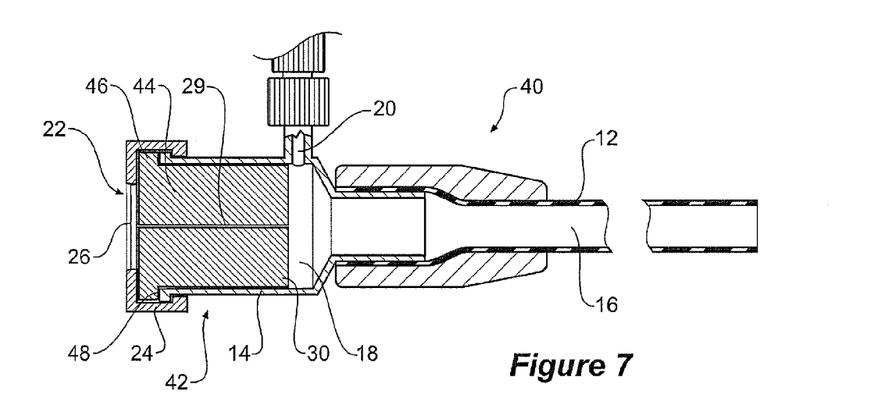
FIG. 7 shows a longitudinal cross sectional view of an alternative embodiment of an endovascular access sheath according to the present invention.
Figure 8:
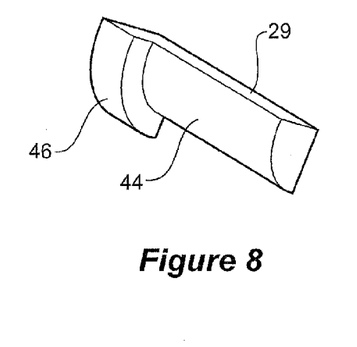
FIG. 8 shows detail of a valve segment suitable for the embodiment of endovascular access sheath shown in FIG. 7.

FIG. 7 shows a longitudinal cross sectional view of an alternative embodiment of an endovascular access sheath 40 according to the present invention and FIG. 8 shows detail of a valve segment suitable for the embodiment of endovascular access sheath shown in FIG. 7. In these drawings the same reference numerals are used for corresponding items to those in FIGS. 1 to 5.

The access sheath 40 comprises a sheath 12 which is mounted into a housing 14 such that a lumen 16 in the sheath 12 is in fluid communication with a housing lumen 18 in the housing 14. The sheath is formed from a flexible lubricious material such as a polyurethane and may be coated with PTFE. The sheath may be of any desired diameter depending upon its intended application and may be, for instance, 12 French.

The housing 14 has a flushing port 20 which provides fluid access to the housing lumen and sheath lumen to allow fluid flushing in use. The housing 14 has an open end 22 and a retaining cap 24 fits over the open end 22. The cap 24 has an access port or aperture 26. The cap is a snap fit onto the housing but may alternatively be a screw or push fit.

Within the housing at the end 22 is a substantially cylindrical valve assembly 42 which is formed from a plurality of valve pieces 44, in this case four valve pieces 44. Each valve piece or valve segment 44 comprises an elongate body being in cross section a sector of a circle with a quarter circle flange 46 extending out radially from one end. A plurality of valve segments when assembled form the substantially cylindrical valve assembly 42. Each valve segment is formed from a resilient material such as a soft silicone rubber.

The valve segments are retained in the housing 14 by the respective flanges 46 being engaged against an annular end surface 48 of the housing and held in place by the cap 24 engaging against the flanges 46.

The valve segments 44 define between each other a series of resilient interfacial regions 29. By this is meant that the interfacial regions are tight together and provide a seal against blood loss through the hemostatic valve but the valve segments can be separated by something placed between them and then grip that thing and the valve segments as far as possible will seal around the thing placed between them. The thing may be for instance a guide wire, a handle for a laparoscopic tool, a lead for a medical device to be used in a laparoscopic procedure or the like.

Figure 9:
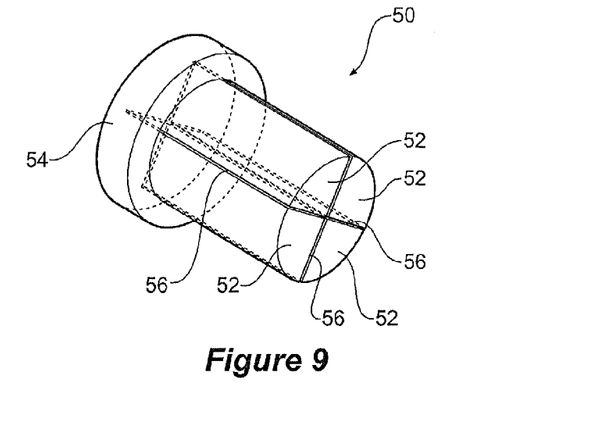
FIG. 9 shows an alternative embodiment of a cylindrical valve assembly according to the present invention.

FIG. 9 shows an alternative embodiment of a cylindrical valve assembly according to the present invention. In this embodiment the four valve segments 52 of the cylindrical valve assembly 50 are held together by an integrally formed circular annular flange 54 at one end of the cylindrical valve assembly. In use this embodiment of the cylindrical valve assembly the flange 54 is engaged against an annular end surface 48 (see FIG. 7) of the housing and held in place by the cap 24 engaging against the flange 54.

In this embodiment the cylindrical valve assembly can be formed as a single component and the slits 56 cut into the component to define between each so defined segment the series of resilient interfacial regions into which a guide wire, for instance, can be received. It will be noted that the slits 56 extend right through the flange 54.

Figure 10:
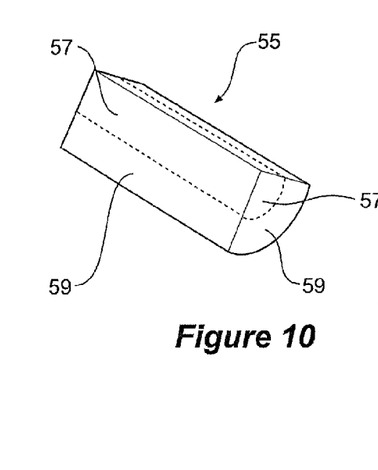
FIG. 10 shows detail of a valve segment of a further embodiment of the present invention.

FIG. 10 shows detail of a valve segment of a further embodiment of the present invention. In this embodiment the valve segment 55 is formed from resilient material of two different densities or hardnesses. An inner portion 57 of the valve segment 55 comprises a part cylindrical portion and is formed from a more dense or harder material and the outer portion 59 of the valve segment 55 comprises a part annular portion and is formed from a less dense or softer material. With this arrangement when the wire is pulled into a slot between adjacent segments such as the slot 29 in FIG. 1 then it will pass along that portion of the slot between the harder portions of the valve segments and into the that portion of the slot between the softer portions of the valve segments and will not tend to migrate back along the slot back towards the centre of the cylindrical valve assembly.

The inner and outer portion can be co-moulded or one of the portions can be moulded over or within the other portion. Alternatively they can be moulded separately and joined together with an adhesive or similar.

Figure 11:
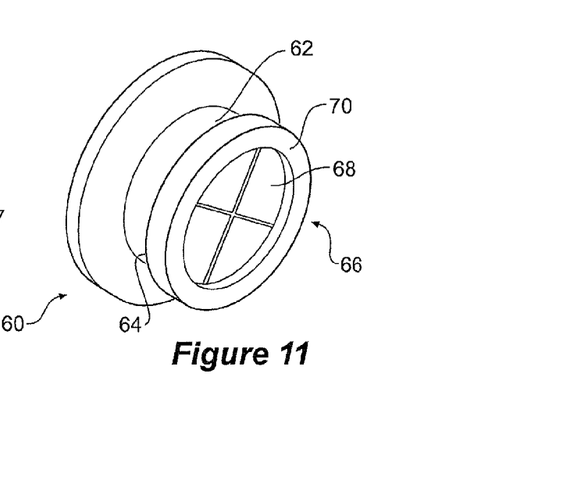
FIG. 11 shows a laparoscopic port according to an embodiment of the present invention.

FIG. 11 shows a laparoscopic port according to an embodiment of the present invention.

Laparoscopic surgery, also called minimally invasive surgery or keyhole surgery, is a surgical technique in which operations in the abdomen are performed through small incision or a laparoscopic port in the peritoneal wall, for instance, of a patient as opposed to the larger incisions needed in an open procedure. A laparoscopic port seals around instruments passed through the port to maintain insufflation pressure within the abdominal cavity, for instance.

In FIG. 11 the laparoscopic port 60 has an outside sealing surface 62 against which the peritoneal wall, for instance, seals in use and a valve housing 64 and a valve arrangement 66. The valve arrangement is formed from a plurality of valve pieces 68, in this case four valve pieces. Each valve piece or valve segment 68 comprises a body being in cross section a sector of a circle. A plurality of valve segments when assembled form the substantially cylindrical valve. Each valve segment is formed from a resilient material such as a soft silicone rubber. The valve segments are retained in the housing 64 by being engaged against an annular end surface within the housing (not shown) and held in place by the cap 70. Where multiple instruments are used through the laparoscopic port one can be moved into one of the slits formed within the valve arrangement and retained there while another of the instruments are being used.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. An access port and sheath assembly comprising a sheath and a haemostatic valve connected with the sheath, the haemostatic valve comprising a housing and a substantially cylindrical valve assembly in the housing, the substantially cylindrical valve assembly having a length and a diameter and wherein the length is at least the same as or greater than the diameter, the cylindrical valve assembly comprising four valve segments, each valve segment comprising a substantially quarter of a circle in cross section, each valve segment comprising an elongate body being in cross section a sector of a circle, whereby the plurality of valve segments when assembled form the substantially cylindrical valve assembly, each valve segment being formed from a resilient material.

2. An access port and sheath assembly as in claim 1 wherein each valve segment is formed from a silicone rubber.

3. An access port and sheath assembly as in claim 1 wherein each valve segment comprises an inner part cylindrical portion and an outer annular portion, the inner portion and the outer portion being joined together, the inner portion being formed from a material which is harder or more dense than the material of the outer portion.

4. An access port and sheath assembly as in claim 1 further including a flushing port in the housing.

5. An access port and sheath assembly as in claim 1 wherein the sheath is a flexible sheath.

6. An access port and sheath assembly as in claim 1 wherein the length of the substantially cylindrical valve assembly is from one to two times the diameter of the substantially cylindrical valve assembly.

7. An access port and sheath assembly as in claim 1 wherein each of the plurality of valve segments comprises an elongate body being in cross section a sector of a circle with a sector of a circle flange extending out radially from one end thereof.

8. An access port and sheath assembly as in claim 1 wherein the cylindrical valve assembly comprises the plurality of valve segments and a circular flange extending out radially from one end thereof and joining the valve segments.

9. An endovascular access port and sheath assembly comprising a sheath and a haemostatic valve;
the sheath comprising an elongate tubular body and a sheath lumen therethrough;
the haemostatic valve comprising a housing, the housing comprising a tubular body with an internal lumen and a first end and a second end, the first end being connected to the sheath and the sheath lumen and the internal lumen being in fluid communication, the second end of the housing comprising an access port;
a substantially cylindrical valve assembly within the housing at the second end of the housing and closing the access port, the substantially cylindrical valve assembly comprising four valve segments, each valve segment comprising an elongate body being in cross section a quarter of a circle, each valve segment being formed from a resilient material, whereby the four valve segments when assembled form the substantially cylindrical valve assembly and defining between adjacent valve segments a plurality of resilient interface regions to receive and grip a device therebetween in use.

10. An access port and sheath assembly as in claim 9 wherein each valve segment is formed from a silicone rubber.

11. An access port and sheath assembly as in claim 9 wherein the substantially cylindrical valve assembly formed from the plurality of valve segments has a length and a diameter and the length is at least the same as the diameter.

12. An access port and sheath assembly as in claim 11 wherein the length of the substantially cylindrical valve assembly is from one to two times the diameter of the substantially cylindrical valve assembly.

13. An access port and sheath assembly as in claim 9 wherein each of the four valve segments comprises an elongate body being in cross section a sector of a circle with a quarter circle flange extending out radially from one end thereof.

14. An access port and sheath assembly as in claim 9 wherein the cylindrical valve assembly comprises the plurality of valve segments and a circular flange extending out radially from one end thereof and joining the valve segments.

15. A laparoscopic port,
the laparoscopic port comprising a haemostatic valve;
the haemostatic valve comprising a housing, the housing comprising a tubular body with an internal lumen and a first end and a second end, the first end of the housing comprising an access port;
a substantially cylindrical valve assembly within the housing at the first end of the housing, the substantially cylindrical valve assembly having a length and a diameter and wherein the length is at least the same as or greater than the diameter, the cylindrical valve assembly comprising four valve segments, each valve segment comprising a substantially quarter of a circle in cross section, each valve segment comprising an elongate body being in cross section a sector of a circle, each valve segment being formed from a resilient material, whereby the plurality of valve segments when assembled form the substantially cylindrical valve assembly and defining between adjacent valve segments a plurality of resilient interface regions to receive and grip a medical device therebetween in use.

* * * * *